(12) United States Patent
Kennedy, II (10) Patent No.: US 7,641,646 B2
(45) Date of Patent: Jan. 5, 2010

(54) CATHETER APERTURE WITH ATTACHABLE STRUCTURE

(75) Inventor: Kenneth C. Kennedy, II, Clemmons, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 64 days.

(21) Appl. No.: 11/705,325

(22) Filed: Feb. 12, 2007

(65) Prior Publication Data

US 2007/0191810 A1  Aug. 16, 2007

Related U.S. Application Data

(60) Provisional application No. 60/773,612, filed on Feb. 15, 2006.

(51) Int. Cl.
*A61M 25/00* (2006.01)
*A61M 5/00* (2006.01)

(52) U.S. Cl. ..................................... 604/524; 604/264

(58) Field of Classification Search ............. 604/264, 604/523, 524
See application file for complete search history.

(56) References Cited

U.S. PATENT DOCUMENTS

| | | | |
|---|---|---|---|
| 5,324,259 A | 6/1994 | Taylor et al. |
| 5,389,087 A | 2/1995 | Miraki |
| 6,190,358 B1 | 2/2001 | Fitzmaurice et al. |
| 6,221,049 B1 | 4/2001 | Selmon et al. |
| 6,346,093 B1 | 2/2002 | Allman et al. |
| 2004/0147908 A1 | 7/2004 | Duffy |

FOREIGN PATENT DOCUMENTS

WO  WO 2006/062873 A1  6/2006

*Primary Examiner*—Victoria Campbell
(74) *Attorney, Agent, or Firm*—Brinks Hofer Gilson & Lione (57) ABSTRACT

An elongate catheter shaft is provided, having a side port aperture through a side wall of the catheter shaft between proximal and distal ends of the shaft. The side port aperture is open to a lumen. Embodiments of the present invention are directed to attached structures disposed in the side port aperture. The attached structures described herein are directed to biasing the catheter shaft in the region of a side port aperture in a straight or curved configuration that resists undesired flexure in the region of the side port aperture and to providing ease of wire guide passage.

13 Claims, 8 Drawing Sheets

CATHETER APERTURE WITH ATTACHABLE STRUCTURE

CROSS-REFERENCE TO RELATED APPLICATIONS

This application claims priority to U.S. Provisional Application Ser. No. 60/773,612, filed Feb. 15, 2006, which is incorporated herein by reference in its entirety.

TECHNICAL FIELD

The present application relates to medical catheters. The present application relates more specifically to medical catheters having a wire guide lumen and a side port aperture that is useful for introduction of a wire guide into the lumen in a configuration commonly known as "rapid exchange," "short wire guide," or "monorail", and that is also useful for other applications in minimally invasive surgical procedures. In particular the present application relates to methods and structures for forming a side port aperture in a catheter shaft and reinforcing the catheter shaft in the region of the side port aperture by use of an overlay or insert.

BACKGROUND

Medical delivery catheters are well known in the art of minimally invasive surgery for introduction of fluids and devices to sites inside a patient's body. A well-established technique, known as "long wire guide," for guiding a delivery catheter to a target site in a patient body includes: (1) positioning a wire guide along a desired path to the target site; (2) retaining a proximal portion of the wire guide outside the body; (3) threading the delivery catheter, which has a wire guide lumen throughout its length, onto the proximal end of the wire guide; and (4) advancing the catheter along the wire guide to the treatment site.

One example of a desired path to a target site is the passage through a working lumen or channel of an endoscope to a biliary duct in a. gastroenterological application. Another example of a desired path is through an endovascular lumen to an occluded coronary artery in a cardiological application. The delivery catheter may have a treatment device such as a stent or fluid-inflatable balloon disposed at its distal end for deployment at a target site (e.g., an occluded biliary duct or coronary artery). The catheter may also have a tool such as a cutting wire or cutting needle disposed at or near its distal end (e.g., a papillotome, sphincterotome, etc.), or the catheter may have an aperture for the delivery of a fluid through a second lumen (e.g., radio-opaque fluid for contrast fluoroscopy, adhesive or gelling agent for delivery to a target site, etc.).

Procedures that employ wire guides often require exchange of treatment appliances. For example, a balloon catheter may be replaced with a stent deployment catheter. In a typical application of such a procedure, a balloon catheter is directed to the site of a stenosis (e.g. in an artery, biliary duct, or other body lumen) as described above. Fluid is then used to inflate the balloon so as to dilate the stenosis. Some procedures are effectively concluded at this point. However, many procedures follow dilation of the stenotic stricture with the placement of a stent to maintain patency of the re-opened lumen. This requires that the balloon catheter be withdrawn to allow introduction of a stent-deployment catheter. It is preferable that the wire guide remain in place for guidance of the stent-deployment catheter without having to re-navigate the wire guide back into to the newly re-opened lumen.

In order to prevent undesired displacement of the wire guide, any exchange of long wire guide catheters requires that the proximal portion of the wire guide extending out of the patient's body (or endoscope, depending on the entry point for the desired path to the target site) must be longer than the catheter being "exchanged out" so that control of the wire guide may be maintained as the catheter is being removed. Likewise, the wire guide must be grasped while the entire catheter being "exchanged in" is threaded onto it and directed along the desired path to the target site. In other words, for the operating physician and assistant to be able to hold the wire guide in place while removing one catheter for replacement with another, each of the catheters must be shorter than the portion of the wire guide that is exposed outside the patient's body (and, if used, outside the endoscope). Put another way, the wire guide must be about twice as long as a catheter that is being used over that wire guide. Additionally, in the case of gastrointestinal endoscopy, even more wire guide length is necessary. This is because the shaft of the endoscope through which the wire guide and catheters are placed must have a length outside the body for manipulation and control, and the catheter itself must have some additional length outside of the endoscope for the same reason. As those skilled in the art will appreciate, wire guides having the necessary "exchange length" are cumbersome and difficult to prevent from becoming contaminated.

An alternative technique for guiding a delivery catheter to a target site in a patient body utilizes catheters having a relatively short wire guide lumen in catheter systems commonly referred to as "rapid exchange," "short wire guide," or "monorail" systems. In such systems, the wire guide lumen extends only from a first lumen opening spaced a short distance from the distal end of the catheter to a second lumen opening at or near the distal end of the catheter. As a result, the only lumenal contact between the catheter's wire guide lumen and the wire guide itself is the relatively short distance between the first and second lumen openings. Several known advantages are conferred by this configuration. For example, the portion of the wire guide outside the patient's body may be significantly shorter than that needed for the "long wire configuration." This is because only the wire guide lumen portion of the catheter is threaded onto the wire guide before directing the catheter through the desired path (e.g., a working lumen of an endoscope, an endolumenal passage, etc.) to the target site.

Figures 1A, 1B:
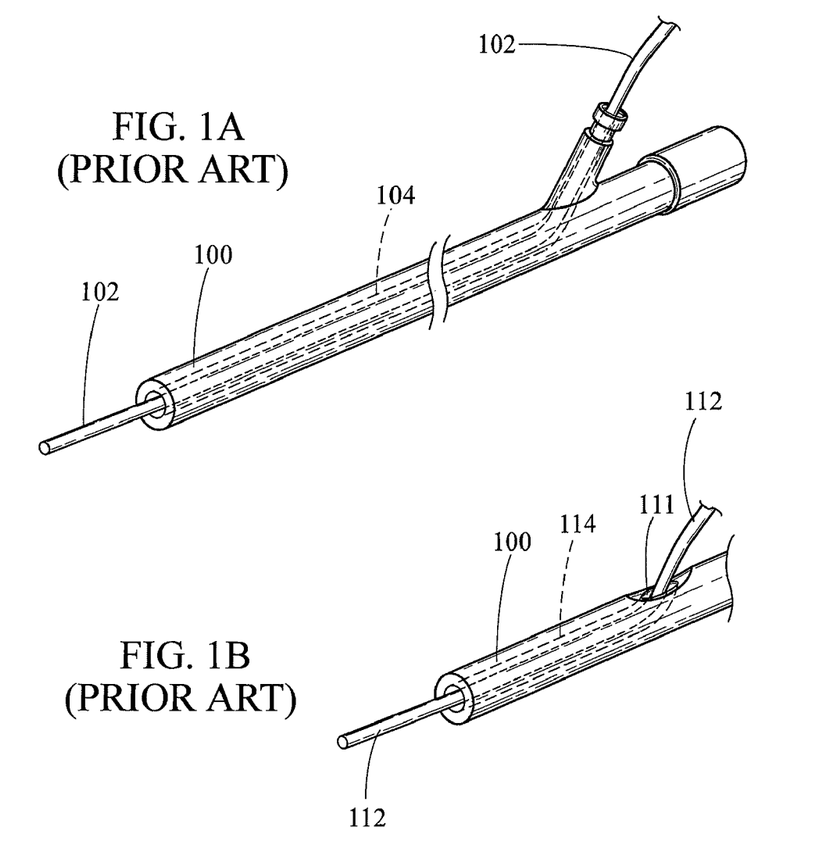
FIG. 1A illustrates a typical prior art long-wire catheter shaft.
FIG. 1B illustrates the distal portion of a typical prior art short-wire catheter shaft.

By way of illustration, the prior art pictured in FIGS. 1A and 1B illustrate the distal ends of two different types of typical catheters. FIG. 1A shows the distal end of a prior art long-wire catheter shaft 100 with a wire guide 102 disposed in a lumen 104. The lumen 104 extends substantially to the proximal end of the catheter shaft 100. (Note: The wire guides illustrated throughout this specification are drawn to illustrate the concepts being described and may not be shown to scale; preferred wire guides typically have an outer diameter that is nearly the same as the inner diameter of catheter lumens through which they are passed.)

FIG. 1B shows the distal end of a prior art short-wire catheter shaft 110 with a side port aperture 111 and a wire guide 112 disposed in a lumen 114. The length of the lumen 114 used by the wire guide, and consequently the exchange length of the catheter 110, is substantially shorter than that of the catheter 100 shown in FIG. 1A. In addition to a shorter exchange length, the catheter 110 (FIG. 1B) has a reduced surface contact between the wire guide and catheter lumen that results in a reduced friction between the two. This can result in an eased threading and exchange process by reducing the time and space needed for catheter exchange. This economy of time and space is advantageous for minimally invasive surgeries by reducing the likelihood of contamination and reducing the total time and stress of completing surgical procedures.

In certain rapid exchange catheter configurations, the wire guide lumen is open to a side port aperture in the side of the catheter between its proximal and distal ends. In one such configuration, the wire guide lumen only extends from the side port aperture to an opening at the distal end. The rapid exchange catheter illustrated in FIG. 1B is one example of this catheter type.

Figure 1C:
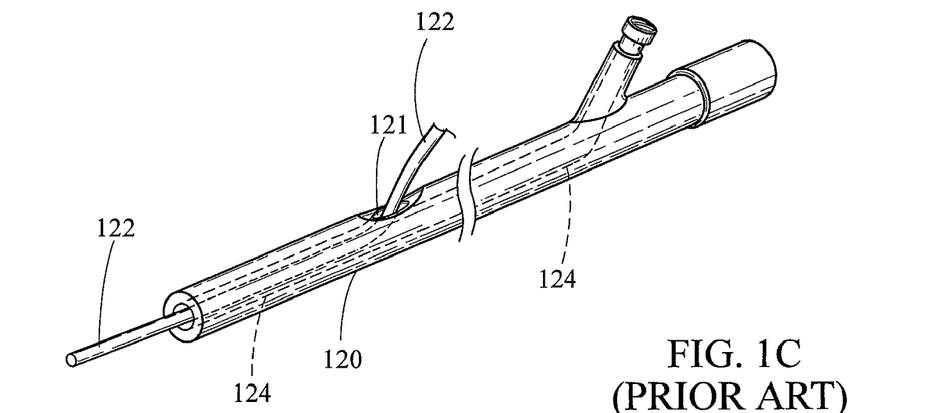
FIG. 1C illustrates a typical convertible catheter shaft.

In another type of rapid exchange catheter configuration, the wire guide lumen extends through the length of the catheter from near its proximal end to its distal end. A side port aperture between the proximal and distal ends opens into the wire guide lumen. This side port aperture allows the catheter to be used in a short wire guide configuration, while the full-length wire guide lumen allows the catheter to be used in a long wire guide configuration. This wire guide lumen configuration is referred to as "convertible" or "dual use." An example of this type of catheter is illustrated in FIG. 1C, which shows a "convertible" catheter shaft 120 with a wire guide 122 disposed through a side port aperture 121 in a distal portion thereof and into a wire guide lumen 124. Specifically, a wire guide 122 may extend through substantially the entire length of the wire guide lumen 124, or the wire guide may extend only through a portion of the lumen 124 between the distal end and the side port aperture 121 (as is illustrated in FIG. 1C).

One common method of producing a side port aperture is by "skiving"—passing a cutter across a catheter surface in a direction transverse to the catheter's longitudinal axis. As shown in the perspective view of a catheter 180 in FIG. 1D, when a semicircular or circular cutter is used to make such a transverse cut, the skived out portion forms a generally elliptical side port aperture 182 that is open to a first lumen 184, which extends generally parallel to the catheter's longitudinal axis. The side port aperture 182 is not open to a second lumen 186, which extends longitudinally through the portion of the catheter 180 opposite the aperture 182.

Figure 1D:
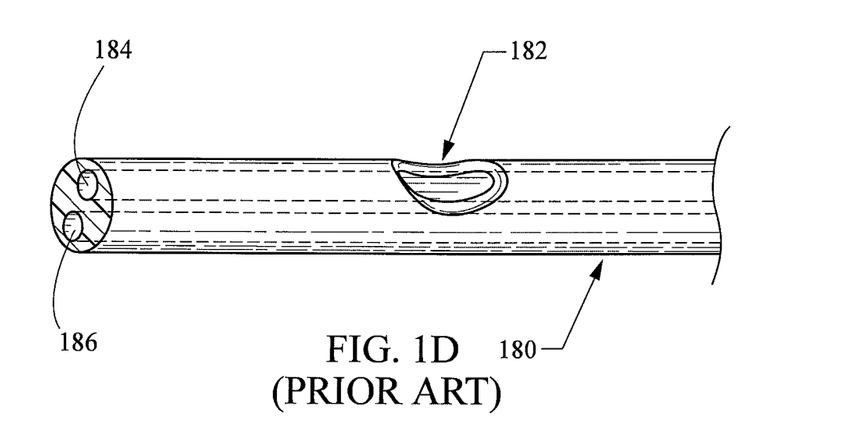
FIG. 1D depicts a perspective view of a typical catheter with a generally elliptical side port aperture.
Figure 1E:
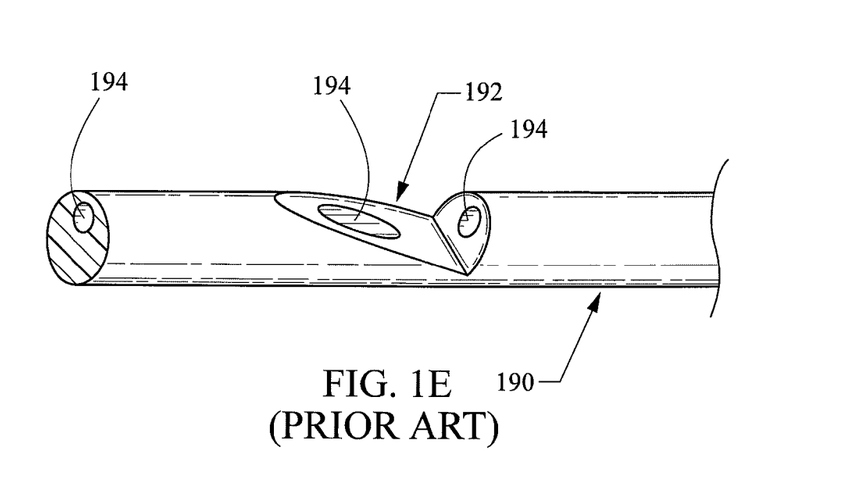
FIG. 1E shows a perspective view of a typical catheter with a generally wedge-shaped or ungular side port aperture.

FIG. 1E shows a catheter 190, wherein the side port aperture 192 was made using an L-shaped cutter or multiple straight cuts to skive out a wedge-like portion of the catheter 190. When the catheter 192 is generally cylindrical, the shape of this wedge-like side port aperture most closely approximates an ungula of a right cylinder. The side port aperture 192 also exposes a longitudinal lumen 194.

Figure 1F:
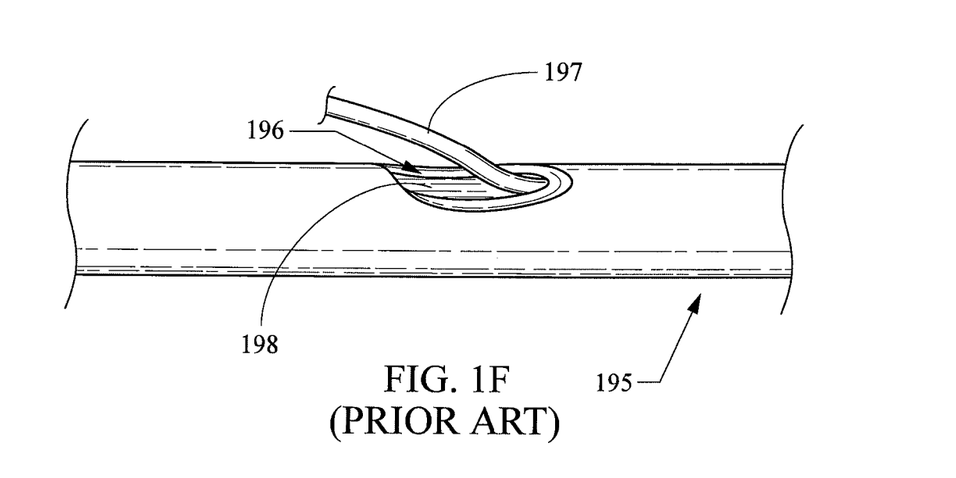
FIG. 1F depicts a perspective view of a typical catheter with a generally elliptical side port aperture and a wire guide passing therethrough.

While offering advantages as explained above, catheter configurations having side port apertures of the type shown illustrated in FIGS. 1D and 1E may be prone to undesirable flexure (e.g., excessive bending, kinking, twisting, or binding) in the region around the aperture. This may often be due to a lack of full columnar support in the region of the side port aperture. For example, and as illustrated in the catheter 195 shown in FIG. 1F, skiving or using other means to create a side port aperture 196 often removes more of the catheter wall than is strictly necessary to allow passage of a wire guide 197 into/out of a lumen 198.

Undesired flexure can have several negative consequences. For example, kinking or excessive flexure of the catheter may cause one or more lumens to be closed off—thereby preventing their use, or may cause a non-smooth edge to be formed adjacent the aperture that could cause damage (e.g., injure an endolumenal passage of a patient or damage the working channel of an endoscope through which the catheter shaft is being passed).

Figure 1G:
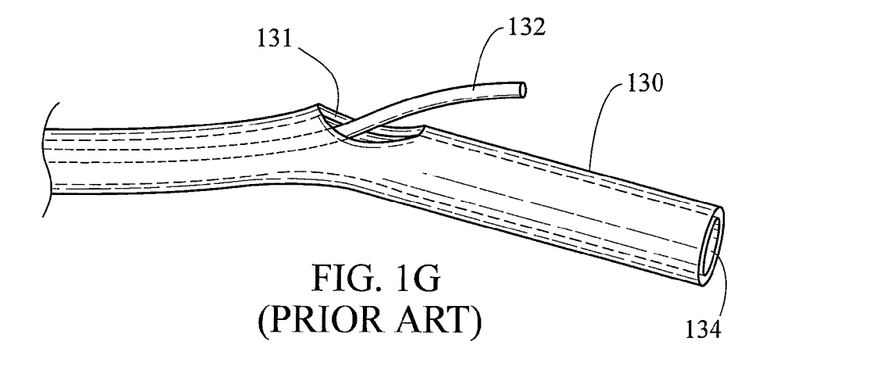
FIG. 1G shows how a wire guide may escape a side port of a typical catheter.

In addition, and as shown in FIG. 1G, a dual use configuration catheter may tend to allow a wire guide 132 being passed from one end through the length of a catheter 130 (particularly if the catheter is bent/curved while in place in the body of a patient being treated) inadvertently to pass out through the side port aperture 131, rather than proceeding to the other end of the wire guide lumen 134. This presents an obvious problem in that a wire guide, to be useful, must exit the wire guide lumen of the catheter via the desired aperture (such as a desired end aperture or another side aperture).

Accordingly, there is a need for a side port aperture configuration that reduces undesirable flexure of the catheter shaft in the region near the side port aperture providing access into the lumen of the catheter. There is a further need for side port aperture that, in a dual use catheter, is configured such that a wire guide being directed from the proximal end through the wire guide lumen has a reduced likelihood of exiting out through the side port aperture.

There is also a need for a method of manufacturing a catheter having a side port aperture that permits greater precision and variety in the formation and configuration of the aperture than is possible with conventional methods.

BRIEF SUMMARY

In one aspect, the present invention includes a catheter having an elongate shaft with proximal and distal ends, a first lumen extending through at least a portion of the shaft and defined by a wall of the shaft, an aperture located between the proximal and distal ends of the shaft and open through the wall to the first lumen, and an attached structure (e.g., an insert or overlay disposed, for example, in, on, or about the aperture).

In another aspect, the present invention includes a method of forming an aperture in a shaft of a catheter for promoting a desired directional passage of a wire guide along a desired path. The method includes the steps of (A) providing a catheter having a shaft comprising a shaft wall and extending between a proximal end and a distal end, and a lumen extending through at least a portion of the shaft. (B) cutting an aperture through the shaft wall at a location between the proximal and distal ends, the aperture being in communication with the lumen; and (C) attaching a reinforcing insert or overlay to the shaft immediately adjacent the aperture.

DETAILED DESCRIPTION OF EXEMPLARY EMBODIMENTS OF THE PRESENT INVENTION

The embodiments of the present invention disclosed herein are generally described in connection with an elongate catheter shaft having a side port aperture through a side wall of the catheter shaft and open to a lumen within the catheter shaft. As used herein, the "side port aperture" or "aperture" refers to the entire open region provided when a portion of catheter shaft is removed to expose a catheter lumen. Embodiments of the present invention provide one or more attachable structures disposed in the immediate vicinity of the side port aperture, including within at least a portion of the side port aperture. More specifically, the embodiments disclosed include attachable structures that surround or are immediately to adjacent the side port aperture. As detailed herein, the attachable structures may be disposed on or be continuous with, for example, an exterior surface of the catheter shaft, an interior lumenal surface of the catheter shaft, within a wall of the catheter shaft, or some combination thereof. Preferred attachable structures may be embodied as overlays or inserts and, as described herein, may generally bias the catheter shaft in the region of a side port aperture in a straight or moderately curved configuration that resists undesired flexure, and may also provide structure that eases passage of a wire guide through a side port aperture.

The overlays or inserts described herein may be attached to the catheter by, for example, overmolding, thermal bonding (e.g., heat staking, ultrasonic bonding), adhesive bonding, mechanical attachment (e.g., insert tabs, threaded pins), other suitable attachment means, or combinations thereof. The overlays or inserts described herein may be formed by, for example, plastic injection molding, casting, metal injection molding, machining, lamination, other suitable fabrication means, or combinations thereof. They may be formed independently as prefabricated structures and then attached to a catheter side port aperture, or they may be formed in place on and/or immediately adjacent to a catheter side port aperture. Suitable materials for construction of the catheter overlays or inserts include, for example, polymers, metals, ceramics, composites, materials substantially the same as a material comprising the catheter shaft, particulates, or combinations thereof that will provide a desirable stiffness/flexibility. In the most preferred embodiments, the materials comprising the overlays or inserts have at least some different properties than the adjacent catheter composition. For example, the overlay or insert region may be more flexible or less flexible and/or more lubricious or less lubricious than the catheter. (For example, in a catheter having a durometer between about 70D and 72D, an overlay or insert may have a durometer between about 55A and 55D. By way of example and for purposes of illustration, durometers of about 35A to about 72D are contemplated for polymers used in overlays or inserts.) The overlays or inserts may comprise a lubricious coating (e.g., to ease passage of a wire guide therethrough; to provide a lubricious external and/or internal surface), which may be the same or different than a lubricious coating or surface material of the adjacent catheter. The overlays or inserts may also comprise radio-opaque materials. In certain preferred embodiments, the materials of which an overlay or insert is constructed will provide enhanced stiffness in the region of the side port aperture.

FIGS. 2A-8 illustrate embodiments of catheters and attachable structures of the present invention. For the sake of convenience, in each of the figures, the left side corresponds to proximal and the right side corresponds to distal, with reference to catheter directionality. The catheters shown are portrayed diagrammatically in order to illustrate the overlays and inserts (which may be oriented as shown or rotated proximally-distally 180°), and in actual embodiments the catheter body portions may differ from those illustrated (for example, the proximal and/or distal lengths from the side port may be longer than illustrated, and the distal end of actual catheter embodiments may be relatively longer as well as being tapered and/or rounded). While each embodiment is shown as a plain catheter tube, those of skill in the art will appreciate that embodiments described herein may be used within the scope of the present invention with many catheter devices including, for example, sphincterotomes, balloon catheters, stent-installation catheters, and other currently existing or future-developed catheter devices.

Figure 2A:
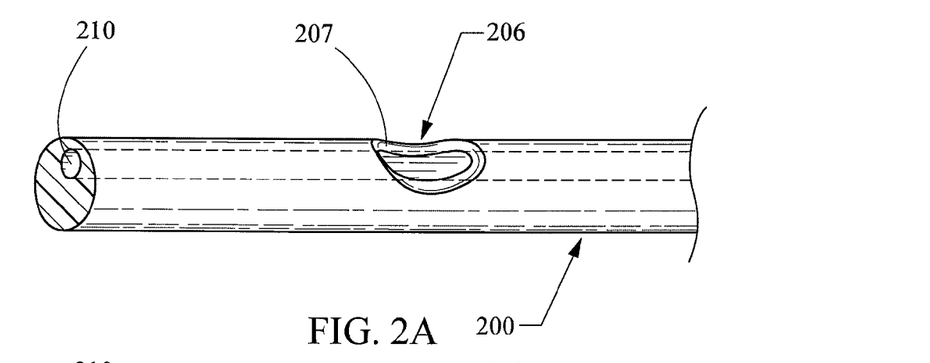
FIG. 2A illustrates an embodiment of a catheter shaft having a generally elliptical side port aperture.
Figure 2B:
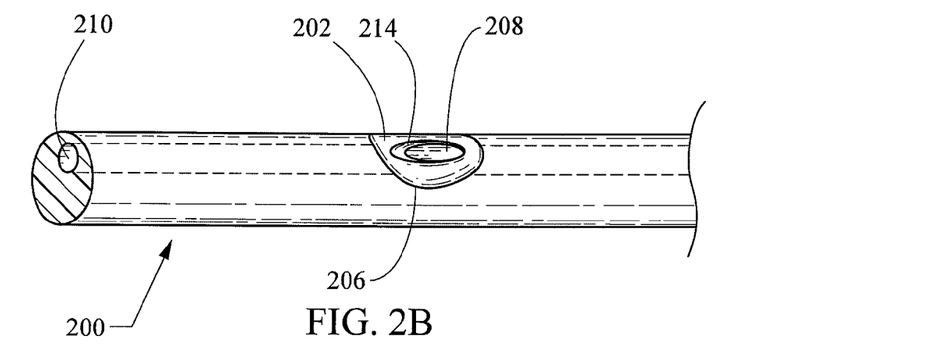
FIG. 2B illustrates the catheter shaft of FIG. 2A with a first overlay embodiment disposed thereon.
Figure 2C:
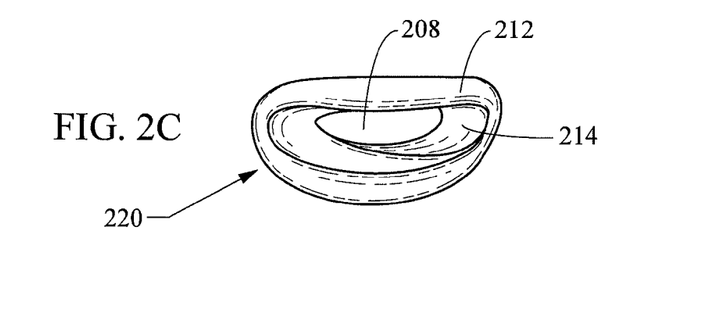
FIG. 2C illustrates a detail view of the overlay embodiment of FIG. 2B.

FIG. 2A shows an embodiment of a catheter shaft 200 having a lumen 210 longitudinally therethrough, with a side port aperture 206 that is defined by a lip 207 and is open to the lumen 210. FIG. 2B illustrates the catheter 200 with an attached stiffening structure comprising a first embodiment of an overlay 202 that is disposed on a surface of the shaft 200 by, for example, adhesive, molding, or some other method of deposition In the particular embodiment illustrated, the overlay 202 is a plastic construction secured by adhesive to the lip 207 of the side port aperture 206. The overlay 202 includes a fenestration embodied as an access port 208, which is smaller in diameter than the side port aperture 206, but is configured to allow transit of a wire guide therethrough. FIG. 2C shows a bottom perspective view of the overlay 202 in greater detail. Preferably, the overlay 202 is sized to fit into the side port aperture 206 of the catheter 200 such that when assembled thereto, the outer profile of the catheter 200 is generally smooth with a generally consistent outer diameter. The overlay 202 includes a lower surface 212 that is curved in a saddle-like shape that preferably is configured to be adhered or otherwise attached to the lip 207. The access port 208 provides an angled surface 214.

As illustrated in FIGS. 2B and 2C, the surface 214 angles generally from a proximal exterior portion of the overlay 202 to a distal portion immediately adjacent the lumen 210. This surface 214 preferably is configured to ease passage of a wire guide through the overlay 202 between the proximal exterior and the distal interior of the catheter 200 (e.g., allowing passage of a wire guide from the distal portion of the lumen 210 out through the access port 208 more readily than an access port having generally vertical sides). The same combination of angled surface 214 and access port 208 preferably is configured to decrease the likelihood of a wire guide being used in a long wire guide configuration of a dual-use/convertible catheter from escaping through the side port aperture 206. Specifically, as depicted in FIGS. 2B-2C, the angle of the surface 214 is such that the approach for a wire guide to the access port 208 is more open for a wire guide approaching from the distal side than from the proximal side.

A method of the present invention is also described with reference to the embodiment shown in FIGS. 2A-2C. The method includes the steps of (A) providing a catheter 200 having a shaft comprising a shaft wall and extending between a proximal end and a distal end, and a lumen 210 extending through at least a portion of the shaft; (B) cutting an aperture 206 through the shaft wall at a location between the proximal and distal ends, the aperture 206 being in communication with the lumen; and (C) attaching a reinforcing insert or overlay (such as, for example, overlay 202) to the shaft immediately adjacent the aperture 202. The reference to the embodiment illustrated in FIGS. 2A-2C is not intended to limit the method, which those of skill in the art will appreciate as being applicable to other embodiments of the present invention.

Figure 3A:
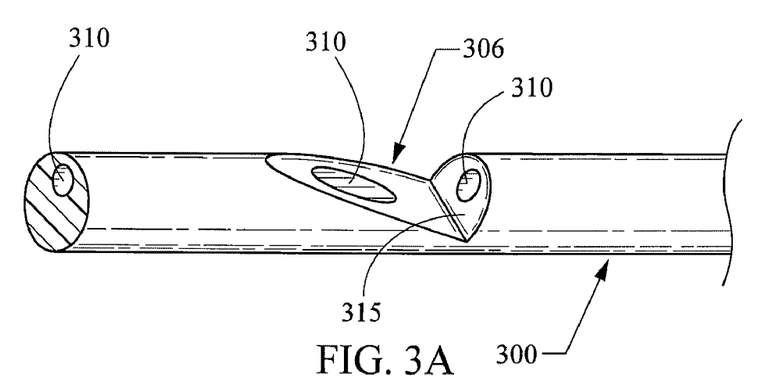
FIG. 3A illustrates an embodiment of a catheter shaft having a wedge-shaped side port aperture.
Figure 3B:
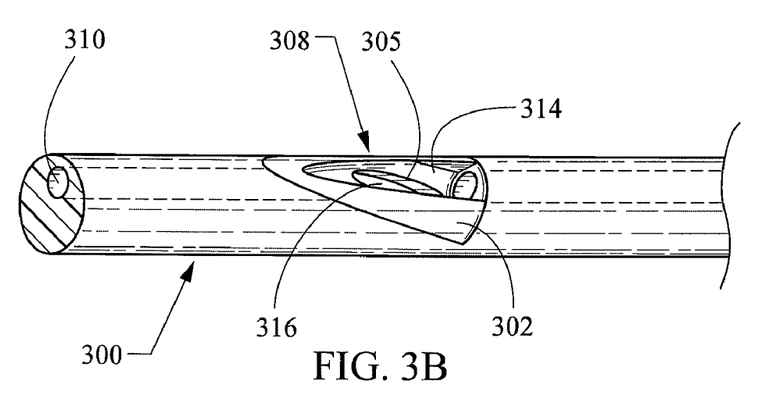
FIG. 3B illustrates the catheter shaft of FIG. 3A with a second overlay embodiment disposed thereon.
Figure 3C:
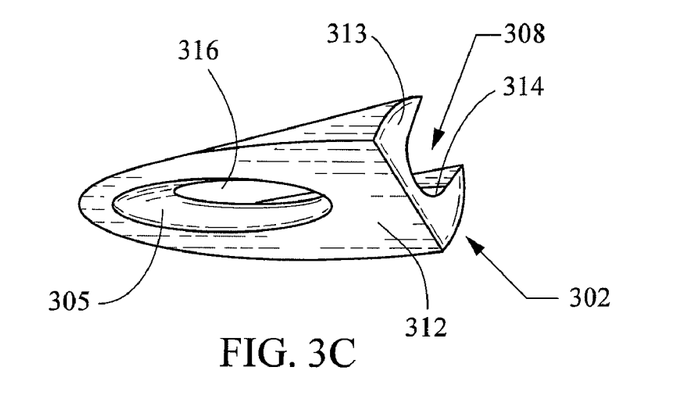
FIG. 3C illustrates a detail view of the overlay embodiment of FIG. 3B.

FIG. 3A shows an embodiment of a catheter shaft 300 having a lumen 310 longitudinally therethrough, with a side port aperture 306 open to the lumen 310. The side port aperture 306 of the catheter 300 is wedge-shaped and provides external access to the lumen 310. As shown in FIG. 3B, a second embodiment of an attached overlay 302 is disposed in the wedge-shaped side port aperture in the surface of the shaft 300. The overlay 302 includes an access port 308, which is smaller than the side port aperture, but which is configured to allow transit of a wire guide, particularly in dual-use/convertible catheter being used in a long-wire configuration. FIG. 3C shows a bottom perspective view of the overlay 302 in greater detail. The access port 308 is aligned with a groove 305, that provides for continuity of the lumen 310 when the overlay 302 is in place on the catheter 300. Preferably, the overlay 302 is sized to fit into the side port aperture of the catheter 300 such that when assembled thereto, the outer profile of the catheter 300 is generally smooth, with a generally consistent diameter. The overlay 302 includes a lower surface 312 and an end surface 313, each of which is configured to contact the catheter wall. The access port 308 provides an angled surface 314 configured to ease passage of a wire guide through the overlay 302 between the proximal exterior and the distal interior of the catheter 300 (e.g., allowing passage of a wire guide from the distal portion of the lumen 310 out through the access port 308 more readily than an access port having generally vertical sides). The overlay 302 includes a surface 315 defining a proximal aperture 316. When the overlay 302 is attached to the catheter 300, the surface 315 preferably is substantially parallel to or coaxial with the inner surface of the lumen 310. The proximal aperture 316 is generally aligned and continuous with the lumen 310 and preferably is configured to allow passage of a wire guide when the catheter 300 is used in a long-wire configuration (i.e., the wire guide passes from the proximal portion of the lumen 310 through the proximal aperture 316 and continues through the distal portion of the lumen 310 without exiting through the access port 308).

Figure 4A:
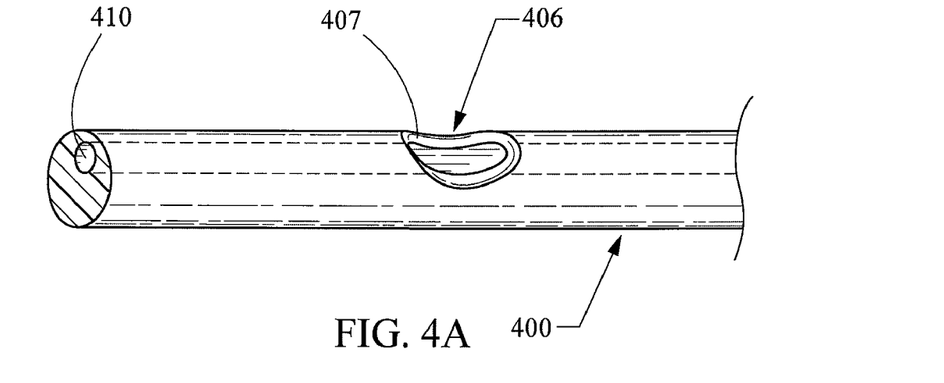
FIG. 4A illustrates an embodiment of a catheter shaft having a generally elliptical side port aperture.
Figure 4B:
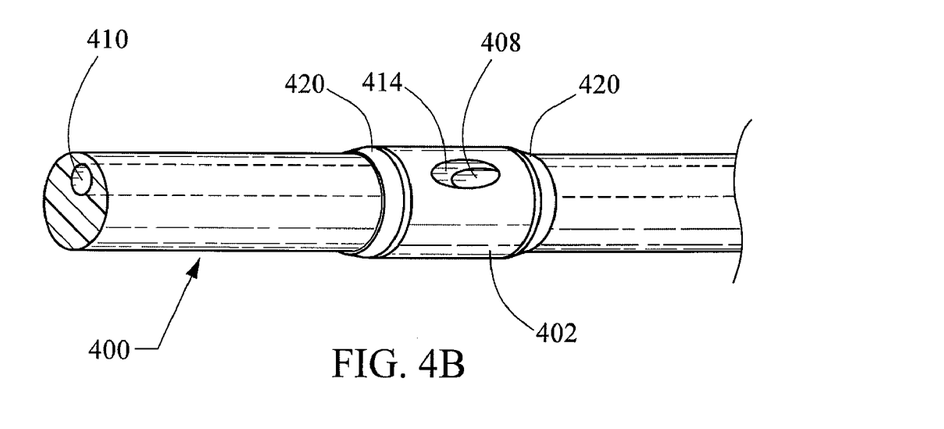
FIG. 4B illustrates the catheter shaft of FIG. 4A with a third overlay embodiment disposed thereon.
Figure 4C:
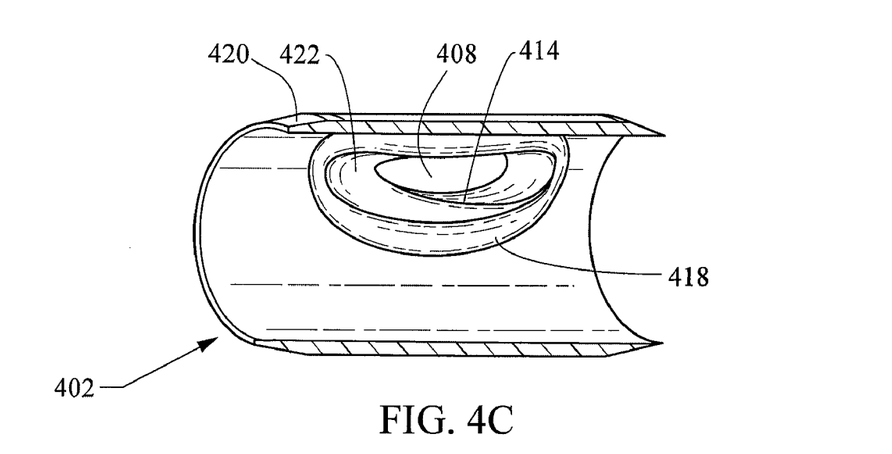
FIG. 4C illustrates a detail view of the overlay embodiment of FIG. 4B.

FIG. 4A shows an embodiment of a catheter shaft 400 having a lumen 410 longitudinally therethrough with a side port aperture 406 that is defined by a lip 407 and is open to the lumen 410. FIG. 4B illustrates the catheter 400 with an attached structure comprising a third embodiment of an overlay 402 that is disposed on a surface of the shaft 400. The overlay 402 includes an access port 408, which is smaller in diameter than the side port aperture 406, but is configured to allow transit of a wire guide. The ends of the overlay 402 each preferably include a rounded surface 420 so that the overall exterior profile of the assembled catheter and overlay is generally smooth. In alternative embodiments, the rounded surface 420 may be tapered or otherwise shaped in a manner that preferably avoids a stepped junction between the overlay 402 and the catheter shaft 400. FIG. 4C shows a bottom perspective cutaway view of the attachable overlay 402.

Preferably, the overlay 402 is sized to fit around the outer circumference of the catheter 400 and includes a curved underside surface 418 that preferably is contoured to fit the catheter wall contours that form the lip 407 of the side port aperture 406. However, the construction of the overlay 402 advantageously allows for a less precise shape/size when the side port aperture 406 is being made.

The underside of the overlay 402 also includes a curved channel 422 that preferably aligns with the upper contour of the lumen 410 such that the overlay 402 does not significantly occlude the longitudinal path of the catheter lumen 410. As is also visible in FIG. 4B, the access port 408 provides an angled surface 414 configured to ease passage of a wire guide through the access port 408 of the overlay 402. The orientation of the angled surface 414, the curved channel 422, and the access port 408 preferably is configured to decrease the likelihood of a wire guide from escaping through the side port aperture 406 of a dual-use/convertible catheter being used in a long wire guide configuration. This configuration also would ease passage of a wire guide from the distal portion of the lumen 410 out through the access port 408 more readily than an access port having generally vertical sides).

Figure 5A:
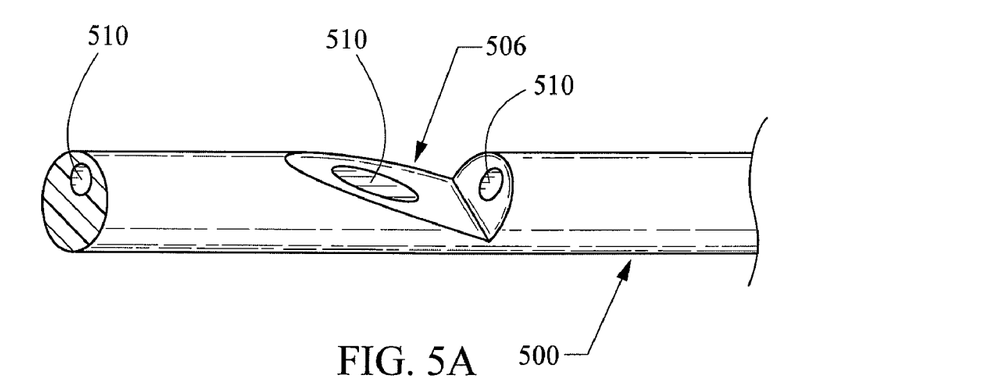
FIG. 5A illustrates an embodiment of a catheter shaft having a wedge-shaped side port aperture.
Figure 5B:
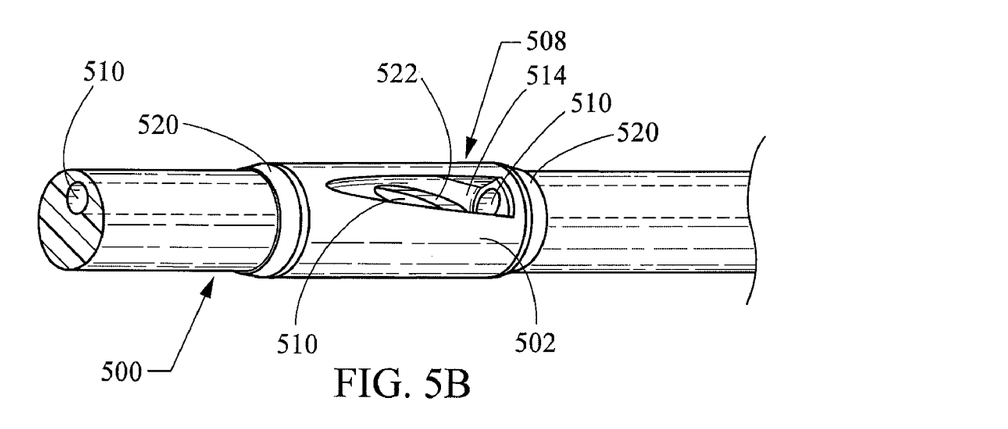
FIG. 5B illustrates the catheter shaft of FIG. 5A with a fourth overlay embodiment disposed thereon.
Figure 5C:
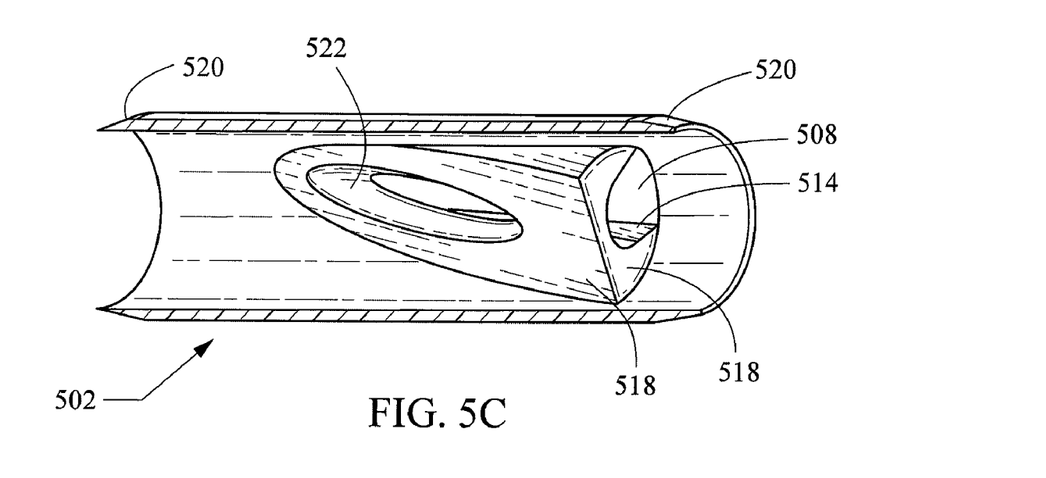
FIG. 5C illustrates a detail view of the overlay embodiment of FIG. 5B.

FIG. 5A shows an embodiment of a catheter shaft 500 having a lumen 510 longitudinally therethrough, with a wedge-shaped side port aperture 506 open to the lumen 510. FIG. 5B illustrates the catheter 500 with an attached stiffening structure comprising a fourth embodiment of an overlay 502 that is disposed on a surface of the shaft 500. The overlay 502 includes an access port 508, which is smaller in size than the side port aperture 506, but is configured to allow transit of a wire guide. The overlay 502 also includes a channel 522 that preferably aligns with the lumen 510 such that the overlay 502 does not significantly occlude the longitudinal path of the catheter lumen 510. The ends of the overlay 502 each preferably include a rounded surface 520 so that the overall exterior profile of the assembled catheter and overlay is generally smooth, even though the overlay 502 has a greater cross-sectional diameter than the catheter 500. FIG. 5C shows a bottom perspective cutaway view of the attachable overlay 502. Preferably, the overlay 502 is sized to fit around the outer circumference of the catheter 500 and includes underside surfaces 518 that are contoured to fit the catheter wall contours of the side port aperture 506. As visible in FIG. 5B, the access port 508 provides an angled surface 514 configured to ease passage of a wire guide through the access port 508 of the attachable overlay 502.

Figure 6A:
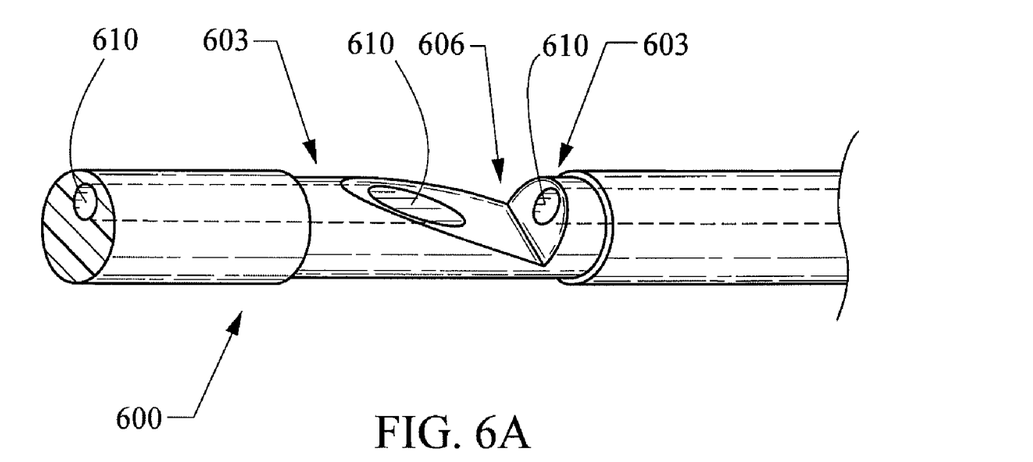
FIG. 6A illustrates an embodiment of a catheter shaft having a wedge-shaped side port aperture.
Figure 6B:
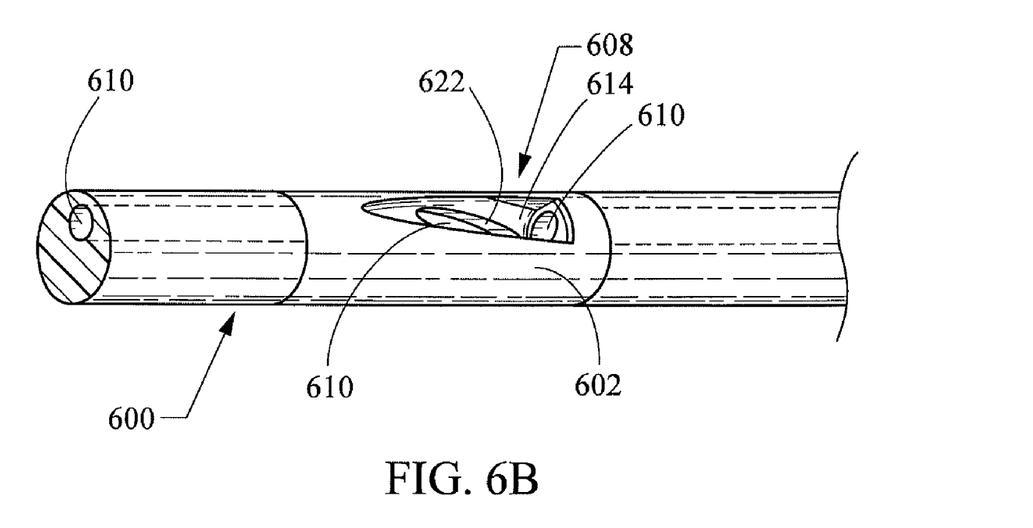
FIG. 6B illustrates the catheter shaft of FIG. 6A with a fifth overlay embodiment disposed thereon.

FIG. 6A shows an embodiment of a catheter shaft 600 having a lumen 610 longitudinally therethrough, with a wedge-shaped side port aperture 606 open to the lumen 610. The catheter 600 has a region of reduced shaft diameter 603 that extends both proximally and distally of the side port aperture 606. This reduced diameter may be produced by chemical, mechanical, or other processes known in the art. FIG. 6B illustrates the catheter 600 with an attached structure comprising a fifth embodiment of an overlay 602 that is disposed on the reduced diameter shaft region 603 such that the catheter 600 has a substantially consistent external diameter. The overlay 602 includes an access port 608, which is smaller in size than the side port aperture 606, but is configured to allow transit of a wire guide. The overlay 602 also includes a channel 622 that preferably aligns with the lumen 610 such that the overlay 602 does not significantly occlude the longitudinal path of the catheter lumen 610. Preferably, the overlay 602 is sized to fit around the outer circumference of the catheter 600 and includes underside surfaces that are contoured to fit the catheter wall contours of the side port aperture 606. As visible in FIG. 6B, the access port 608 provides an angled surface 614 configured to ease passage of a wire guide through the access port 608 of the overlay 602.

Figure 7A:
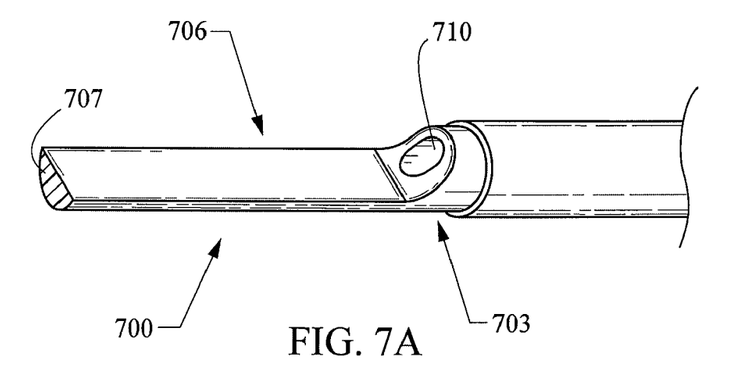
FIG. 7A illustrates an embodiment of a catheter shaft having an elongate side port aperture.
Figure 7B:
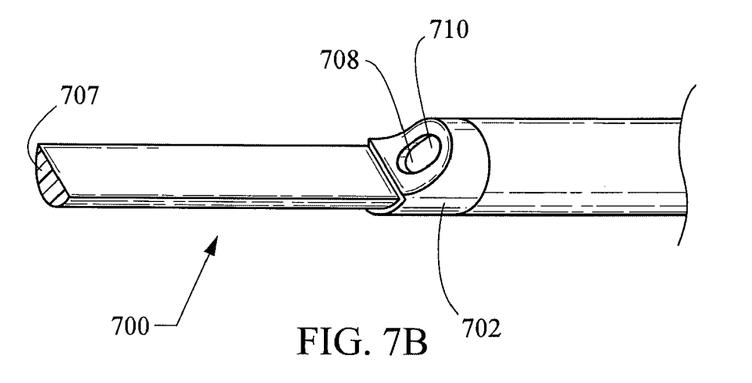
FIG. 7B illustrates the catheter shaft of FIG. 7A with a sixth overlay embodiment disposed thereon.

FIG. 7A shows an embodiment of a catheter shaft 700 having a lumen 710 longitudinally therethrough, with a long side port aperture 706 open to the lumen 710. The long side port aperture 706 is formed by removing a portion of the catheter body, leaving a portion having a generally D-shaped cross-section 707. The catheter 700 has a region of reduced shaft diameter 703 that extends immediately adjacent the side port aperture 706. FIG. 7B illustrates the catheter 700 with an attached structure comprising a sixth embodiment of an overlay 702 that is disposed on the reduced diameter shaft region 703 such that the catheter 700 has a substantially consistent external diameter. The overlay 702 includes an access port 708 that is configured to allow transit of a wire guide.

Figure 8:
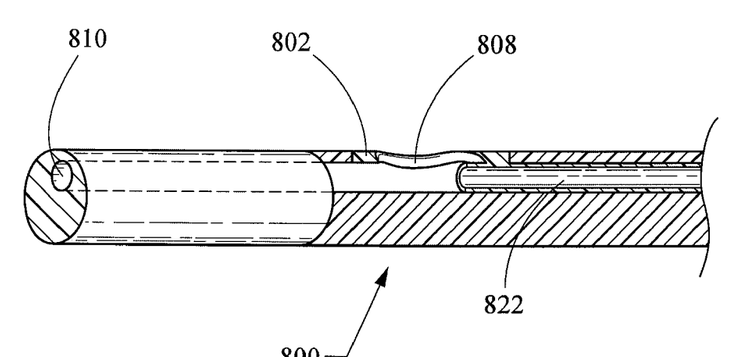
FIG. 8 illustrates a catheter shaft having a generally elliptical side port aperture with an insert disposed therein.

FIG. 8 illustrates a catheter 800 from a perspective view in partial longitudinal cross-section with an attached structure comprising a first embodiment of an insert 802 that is disposed on the shaft 800. The insert 802 includes an access port 808 between the catheter exterior and the lumen 810. The insert 802 preferably is sized and shaped such that the overall exterior profile of the assembled catheter and insert is generally smooth and of a consistent diameter. The insert 802 includes a cannula 822 that extends both proximally and distally into the catheter lumen 810. In alternative embodiments, a cannula may extend either proximally or distally from the insert, as shown in FIG. 8. Those of skill in the art will appreciate that inserts including a cannula may include different sizes and shapes (e.g., adding one or more cannulas to the overlays illustrated in FIGS. 2B, 3B, 4B, 5B, 6B, or 7B, or to another overlay or insert of the present invention).

As illustrated generally by the embodiments illustrated herein, inserts and overlays of the present invention provide a greater variety of sizes, shapes, and configurations for use in providing a side port to a catheter than just incision of the catheter itself. Additionally, a side port aperture cut imprecisely in a catheter may thereafter have an insert or overlay attached to it that provides a precise, desired shape and size configuration for providing access to a lumen of the catheter. The materials and methods appropriate for use with the foregoing embodiments of the present invention but not explained in detail herein will be readily apparent to those skilled in the art. It is therefore intended that the foregoing detailed description be regarded as illustrative rather than limiting, and that it be understood that it is the following claims, including all equivalents, that are intended to define the spirit and scope of this invention.

I claim:

1. A catheter device comprising an elongate shaft, said elongate shaft comprising:
   a proximal end;
   a distal end;
   a first lumen extending through at least a portion of the shaft and defined by a wall;
   an aperture through the wall, open to the first lumen;
   said aperture disposed between the proximal and distal ends, the shaft including at least one continuous portion adjacent the aperture such that the proximal and distal ends include a continuous shaft between them; and
   an overlay disposed at least partially in the aperture, the overlay including an access port open to the first lumen, said access port being configured for passage of a wire guide therethrough, wherein an external diameter of the elongate shaft comprises a consistent external diameter along a shaft length from a region proximal of the overlay through a region distal of the overlay, such that the external shaft diameter along the overlay is no greater than the external shaft diameter immediately proximal of the overlay and immediately distal of the overlay.

2. The catheter device of claim 1, wherein the overlay is constructed comprising a composition selected from a group consisting of polymer, radio-opaque material, metal, composite, ceramic, materials that have substantially the same composition as the shaft, and any combination thereof.

3. The catheter device of claim 1, wherein the overlay comprises a material that is stiffer than material comprised by a shaft region adjacent the overlay.

4. The catheter device of claim 1, wherein the access port of the overlay comprises a surface that is angled from a proximal exterior portion of the overlay to a distal portion of the overlay immediately adjacent the first lumen.

5. The catheter device of claim 1, wherein the access port of the overlay comprises a generally cylindrical passage angled from a more proximal upper portion to a more distal lower portion of the overlay.

6. The catheter device of claim 1, wherein the overlay further comprises an open passage generally continuous with the first lumen.

7. The catheter device of claim 1, wherein the overlay is attached to the catheter device by overmolding, thermal bonding, adhesive bonding, mechanical attachment, or any combination thereof.

8. The catheter device of claim 1, wherein the overlay comprises a prefabricated structure.

9. The catheter device of claim 1, wherein the overlay is fabricated on the elongate shaft.

10. The catheter device of claim 1, wherein the access port is smaller than the aperture.

11. A method of providing a side port aperture with a support structure, comprising the steps of:
   providing an elongate catheter shaft, the catheter shaft comprising a lumen therethrough and a wall surrounding the lumen;
   providing a side port aperture while leaving a shaft portion that is, continuous from proximal to distal of the aperture;
   providing a support structure, the support structure comprising
      a body configured to fit into at least a portion of the side port aperture;
      a fenestration through the body, the fenestration providing an angled path from an upper side of the body therethrough to the lower side; and attaching the support structure to the catheter shaft such that at least a portion of the support structure is disposed in the side port aperture and the fenestration of the support structure provides an opening to the lumen, said fenestration being smaller than the side port aperture, wherein an external diameter of the elongate shaft comprises a consistent external diameter along a shaft length from a region proximal of the support structure through a region distal of the support structure, such that the external shaft diameter along the support structure is no greater than the external shaft diameter immediately proximal of the support structure and immediately distal of the support structure.

12. A catheter device comprising a continuous elongate shaft,
   said elongate shaft comprising:
   a proximal end;
   a distal end;
   a first lumen extending through at least a portion of the shaft and defined by a wall;
   an aperture through the wall, open to the first lumen;
   said aperture disposed between the proximal and distal ends, occupying less than a complete circumference of the continuous shaft;
   an attachment disposed at least partially in the aperture, the attachment comprising an access port open to the first lumen, said access port being configured for passage of a wire guide therethrough, wherein an external diameter of the elongate shaft comprises a consistent external diameter along a shaft length from a region proximal of the attachment through a region distal of the attachment, such that the external shaft diameter along the attachment is no greater than the external shaft diameter immediately proximal of the attachment and immediately distal of the attachment.

13. The catheter device of claim 12, wherein the attachment is a selected one of an insert or an overlay.

* * * * *